US012426898B2

(12) United States Patent
Sharma

(10) Patent No.: US 12,426,898 B2
(45) Date of Patent: Sep. 30, 2025

(54) SYSTEMS FOR USING THE STATUS OF A MOTOR DURING A SURGICAL DRILLING PROCEDURE TO IMPROVE EFFICIENCY OF A BREAKTHROUGH ALGORITHM

(71) Applicant: Stryker Corporation, Kalamazoo, MI (US)

(72) Inventor: Rahul Sharma, Gurgaon (IN)

(73) Assignee: Stryker Corporation, Portage, MI (US)

( * ) Notice: Subject to any disclaimer, the term of this patent is extended or adjusted under 35 U.S.C. 154(b) by 530 days.

(21) Appl. No.: 17/768,173

(22) PCT Filed: Oct. 12, 2020

(86) PCT No.: PCT/US2020/055252
§ 371 (c)(1),
(2) Date: Apr. 11, 2022

(87) PCT Pub. No.: WO2021/072373
PCT Pub. Date: Apr. 15, 2021

(65) Prior Publication Data
US 2023/0338044 A1 Oct. 26, 2023

Related U.S. Application Data

(60) Provisional application No. 62/914,042, filed on Oct. 11, 2019.

(51) Int. Cl.
A61B 17/16 (2006.01)
A61B 90/00 (2016.01)
A61B 17/00 (2006.01)

(52) U.S. Cl.
CPC ...... A61B 17/1626 (2013.01); A61B 17/1622 (2013.01); A61B 17/1628 (2013.01);
(Continued)

(58) Field of Classification Search
CPC ...... A61B 2017/00022; A61B 17/1622; A61B 17/1626; A61B 17/1628; A61B 90/06; A61B 2090/061; A61B 2090/062
See application file for complete search history.

(56) References Cited

U.S. PATENT DOCUMENTS 8,734,153 B2 5/2014 Arzanpour et al.
9,492,181 B2 11/2016 McGinley et al.
(Continued)

FOREIGN PATENT DOCUMENTS

JP 2019503721 A 2/2019
WO 2015006296 A1 1/2015
(Continued)

OTHER PUBLICATIONS

International Search Report for Application No. PCT/US2020/055252 dated Feb. 1, 2021, 3 pages.
(Continued)

Primary Examiner — Larry E Waggle, Jr.
(74) Attorney, Agent, or Firm — Howard & Howard Attorneys PLLC

(57) ABSTRACT

A handheld surgical system includes an instrument, a depth measurement attachment, and a controller. The instrument includes a housing and a motor that is positioned within the housing. The depth measurement attachment is removably coupled to the instrument. The depth measurement attachment includes a first sensor that is configured to provide a vibration signal associated with a vibration of the motor during a drilling process, a second sensor that is configured to provide a displacement signal associated with a displacement of a drill bit during the drilling process, and a controller. The controller is configured to receive the vibration signal and the displacement signal. The controller is also configured to determine a characteristic of the motor based on the vibration signal using an algorithm and determine a
(Continued)

breakthrough event based on the motor characteristic and the displacement signal.

11 Claims, 14 Drawing Sheets

(52) U.S. Cl.
CPC .... *A61B 90/06* (2016.02); *A61B 2017/00022* (2013.01); *A61B 2090/062* (2016.02)

(56) References Cited

U.S. PATENT DOCUMENTS

| | | |
|---|---|---|
| 10,159,495 B1 | 12/2018 | Lambert |
| 10,363,050 B2 | 7/2019 | McGinley et al. |
| 10,806,525 B2 | 10/2020 | McGinley et al. |
| 10,893,873 B2 | 1/2021 | McGinley et al. |
| 11,000,292 B2 | 5/2021 | McGinley |
| 11,284,906 B2 | 3/2022 | McGinley et al. |
| 12,004,755 B2 | 6/2024 | Windolf et al. |
| 2005/0116673 A1* | 6/2005 | Carl .................. A61B 17/1626 318/432 |
| 2012/0053492 A1 | 3/2012 | Chang et al. |
| 2015/0201918 A1 | 7/2015 | Kumar et al. |
| 2016/0361070 A1* | 12/2016 | Ardel ................. A61B 17/1617 |
| 2019/0029697 A1 | 1/2019 | Anderson et al. |
| 2021/0085343 A1 | 3/2021 | McGinley et al. |
| 2021/0267608 A1 | 9/2021 | McGinley et al. |

FOREIGN PATENT DOCUMENTS

| | | |
|---|---|---|
| WO | 2017040783 A1 | 3/2017 |
| WO | 2019035096 A1 | 2/2019 |
| WO | 2020232413 A2 | 11/2020 |

OTHER PUBLICATIONS

English language abstract for JP 2019-503721 A extracted from espacenet.com database on Jul. 2, 2024, 2 pages.

* cited by examiner

SYSTEMS FOR USING THE STATUS OF A MOTOR DURING A SURGICAL DRILLING PROCEDURE TO IMPROVE EFFICIENCY OF A BREAKTHROUGH ALGORITHM

RELATED APPLICATIONS

The subject patent application is a U.S. National Stage Patent Application which claims priority to and all of the benefits of International Patent Application No. PCT/US2020/055252 which claims priority to U.S. Provisional Patent Application No. 62/914,042, filed on Oct. 11, 2019, the disclosure of which is hereby incorporated by reference.

BACKGROUND

A common practice in orthopedic surgery is to use a plurality of different surgical tools to repair bone trauma, joint damage due to wear, birth defects, damage due to disease, and the like. A non-limiting example of such a tool is a rotary cutting handheld surgical instrument, such as a drill. These hand-held surgical instruments are used to create bore-holes for many different purposes, for example, to place screws to repair a bone fracture trauma with screws to hold a fixator in place. An important part of these surgical procedures is to determine the proper length of screws to use.

A typical method of bore-hole depth determination uses a separate device in the form of a depth gauge that is introduced into the patient's body to measure the depth of the bore-hole. The two significant disadvantages to this protocol are 1) introducing another surgical instrument into the patient's body while maintaining sterility; and 2) increasing the surgical time, leaving the patient exposed to the ambient environment.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a handheld surgical system is described. The handheld surgical system includes an instrument, a depth measurement attachment, and a controller. The instrument includes a housing and a motor positioned within the housing. The depth measurement attachment is removably coupled to the instrument. The depth measurement attachment includes a first sensor that is configured to provide a vibration signal associated with a vibration of the motor during a drilling process and a second sensor that is configured to provide a displacement signal associated with a displacement of a drill bit during the drilling process. The controller is configured to receive the vibration signal and the displacement signal, determine at least one characteristic of the motor based on the vibration signal using an algorithm, and determine a breakthrough event based on the at least one motor characteristic and the displacement signal.

In a feature, a surgical device is described. The surgical device includes a housing, a motor positioned within the housing, a first sensor configured to generate a motor status signal associated with the motor during a drilling process, a second sensor configured to provide a displacement signal associated with a displacement of a drill bit during the drilling process. The surgical device also includes a controller configured to receive the motor status signal and the displacement signal, determine one or more characteristics of the motor, based on the motor status signal, using a predetermined algorithm, and determine a breakthrough event based on a status of the motor and the displacement signal.

In a feature, a depth measurement attachment for sending a drill depth for a handheld surgical system is described. The handheld surgical system comprises an instrument including a housing and a motor positioned in the housing, The depth measurement attachment comprising a component configured to output a motor status signal associated with the motor during a drilling process, a second sensor configured to output a displacement signal associated with a displacement of a drill bit during the drilling process. A controller is configured to receive the motor status signal and the displacement signal, determine whether the motor is generating rotational torque, based on the motor status signal, and determine a breakthrough event based on the motor status signal and the displacement signal.

In a feature, a depth measurement attachment for sending a drill depth for a handheld surgical system is described. The handheld surgical system comprises an instrument including a housing and a motor positioned in the housing. The depth measurement attachment comprising a component configured to generate a displacement signal associated with a displacement of a drill bit during a drilling process. The depth measurement attachment also comprising a controller configured to receive the displacement signal, determine a frequency component of the displacement signal, determine whether the motor is generating rotational torque, based on the frequency component, and determine a breakthrough event based on the frequency component and the displacement signal.

In a feature, a handheld surgical system is described. The handheld surgical system includes an instrument comprising a housing, a motor positioned in the housing, a depth measurement attachment that is removably coupled to the instrument. The depth measurement attachment comprising a component configured to output a motor status signal associated with the motor during a drilling process, a displacement sensor configured to output a displacement signal associated with a displacement of a drill bit during the drilling process. The depth measurement attachment also comprising a controller configured to receive the motor status signal and the displacement signal, determine whether the motor is generating rotational torque, based on the motor status signal, and determine a breakthrough event based on the motor status signal and the displacement signal.

In a feature, a depth measurement attachment for sending a drill depth for a handheld surgical system is described. The handheld surgical system comprises an instrument including a housing and a motor positioned in the housing. The depth measurement attachment comprising a first sensor configured to output a vibration signal associated with a vibration of the motor during a drilling process, and a second sensor configured to output a displacement signal associated with a displacement of a drill bit during the drilling process. The depth measurement attachment also comprising a controller configured to receive the vibration signal and the displacement signal, determine whether the motor is generating rotational torque, based on the vibration signal, and determine a breakthrough event based on the vibration signal and the displacement signal.

In a feature, a handheld surgical instrument is described. The handheld surgical instrument comprising a housing, a motor positioned in the housing, the motor configured to apply rotational torque to a drill bit during a drilling process, a first sensor configured to output a motor status signal associated with the motor during the drilling process, and a second sensor configured to output a displacement signal associated with a displacement of the drill bit during the drilling process. The handheld surgical instrument also comprising a controller configured to receive the motor status signal and the displacement signal, determine whether the motor is generating the rotational torque, based on the motor status signal, and determine a breakthrough event based on the motor status signal and the displacement signal.

In a feature, a method for determining a breakthrough event of a drilling process is described. The method comprising sensing data, with a first sensor and a second sensor, indicative of one or more procedural events and one or more non-procedural events of the drilling process. The one or more procedural events are associated with movement of a drill bit relative to a bone of a patient when a motor is generating rotational torque. The one or more non-procedural events are associated with movement of the drill bit relative to the bone of the patient when the motor is off. The method further comprising determining whether the data corresponds to the one or more procedural events or the one or more non-procedural events. The method further comprising determining the breakthrough event based on the data associated with the one or more procedural events.

In a feature, a method for determining a breakthrough event of a drilling process with a depth measurement attachment for sending a drill depth for a handheld surgical system is described. The handheld surgical system including an instrument including a housing and a motor configured to apply rotational torque to a drill bit positioned in the housing. The depth measurement attachment including a component, a second sensor, and a controller. The method comprising outputting, with the component, a motor status signal associated with the motor during the drilling process, outputting, with the second sensor, a displacement signal associated with a displacement of the drill bit during the drilling process, receiving, with the controller, the motor status signal and the displacement signal, determining, with the controller, whether the motor is generating the rotational torque, based on the motor status signal, and determining, with the controller, the breakthrough event based on the motor status signal and the displacement signal.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Figure 1:
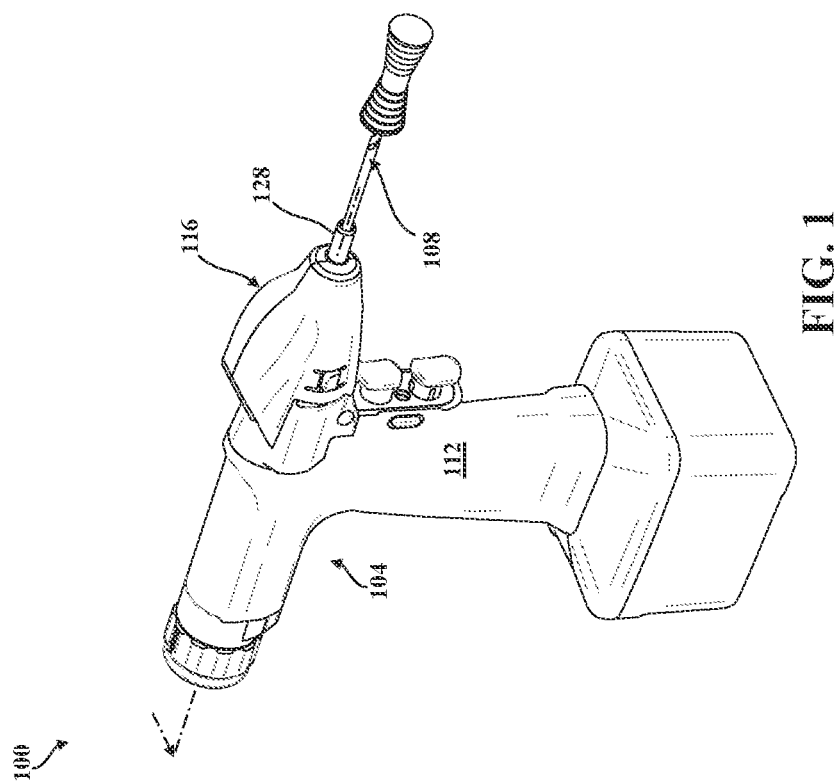
FIG. 1 is a perspective view of a handheld surgical system including an instrument with a depth measurement attachment for drilling a bone according to the teachings of the present disclosure.

With reference to FIGS. 1-5, a handheld surgical system 100 used for performing a surgical drilling procedure is shown. The handheld surgical system 100 eliminates the necessity for a second device such as a depth gauge to determine a bore-hole depth. The handheld surgical system 100 comprises a handheld surgical instrument 104, and a cutting tool 108, such as a drill bit. The handheld surgical instruments discussed in International Patent Publication No. WO2017/040783A1 entitled "Powered Surgical Drill With Integral Depth Gauge That Includes A Probe That Slides Over A Drill Bit" filed on Sep. 1, 2016 and International Patent Publication No. WO2019/035096A1 entitled "Surgical Handpiece For Measuring Depth Of Bore Holes And Relates Accessories" filed on Aug. 17, 2018 are hereby incorporated by reference in their entireties.

The handheld surgical system 100 is configured to determine a depth of a bore-hole that is drilled by the cutting tool 108. The handheld surgical system 100 may also be configured to determine a suitable screw length for bone fixation based on the depth of the bore-hole. The screw length determination may be made immediately after the bone drilling process has been completed. The handheld surgical instrument 104 may comprise a housing 112 and a motor 114 disposed within the housing 112. The housing 112 may have a pistol grip shape or another suitable shape.

Figure 2:
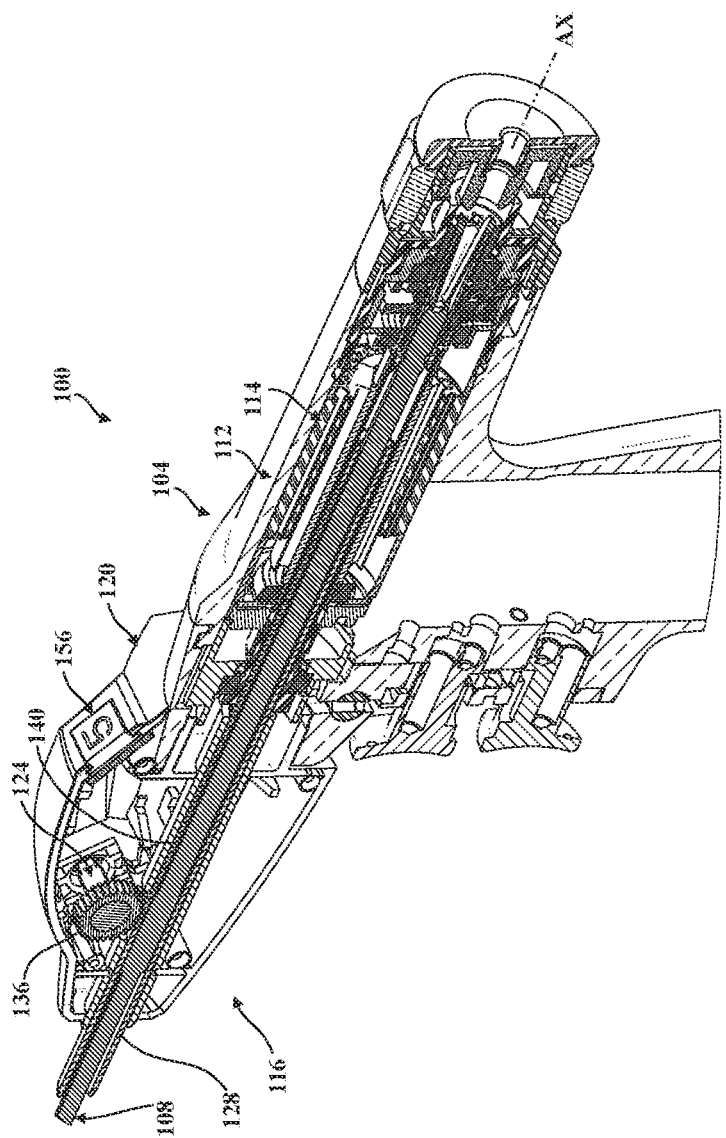
FIG. 2 is a cross-sectional and partial perspective view of a handheld surgical system according to the teachings of the present disclosure with a drill bit inserted therein.
Figure 3:
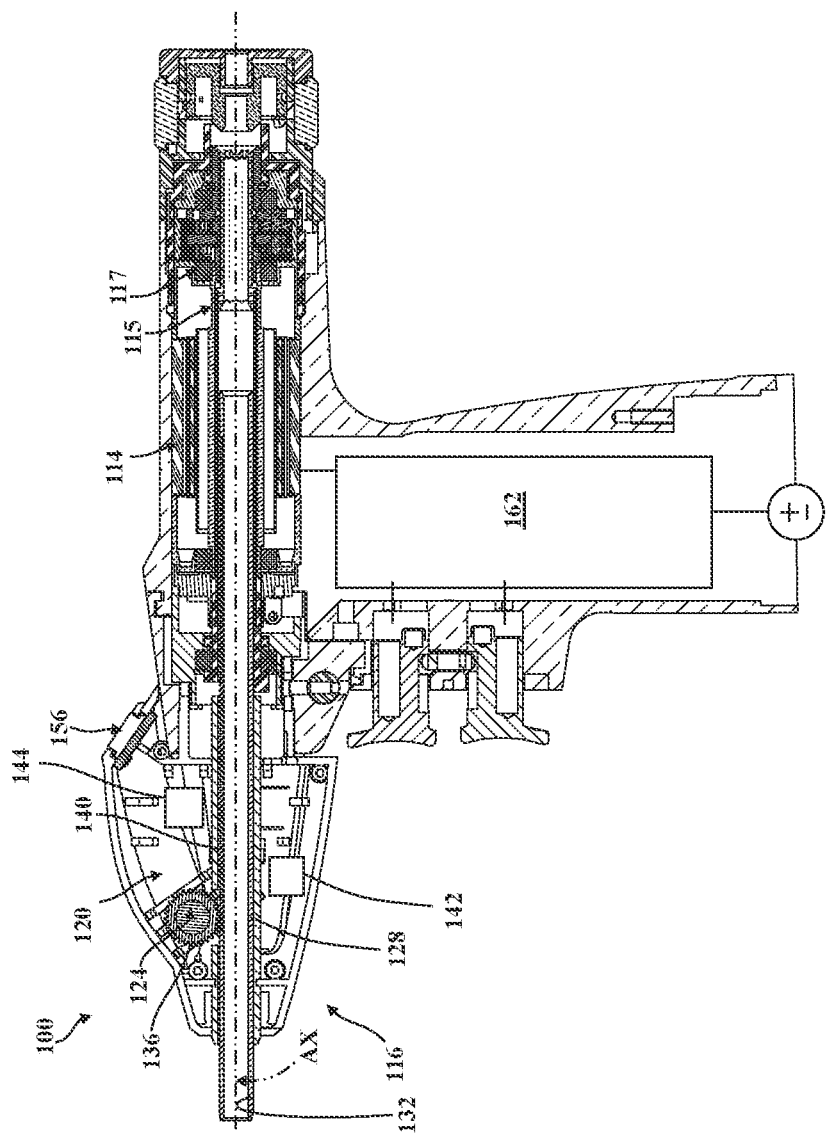
FIG. 3 is a schematic view of a handheld surgical system according to the teachings of the present disclosure.

FIGS. 2 and 3 show the motor 114 positioned along the proximal/distal axis AX within the housing 112, but other motor positions are contemplated. The motor 114 can be electric, pneumatic, or hydraulic. The motor 114 is configured to selectively generate rotational torque in response to commands, signals, and the like received from a controller, such as a second controller 162. The motor 114 comprises a rotor cannula 115 supported for rotation about the axis AX by a pair of bearings 117. A drive gear (not shown in FIG. 3) arranged adjacent to the gearset (not shown in FIG. 3) is coupled to and rotates concurrently with the rotor cannula 115 and is employed to transmit rotational torque to the gearset. For example, the motor 114 and/or gearset configuration discussed in the disclosures WO2017/040783A1 and WO2019/035096A1 may be used as the motor 114 for the handheld surgical system 100.

The handheld surgical system 100 may include a depth measurement attachment 116 that is removably coupled to the housing 112 or integrally formed with the housing 112. The depth measurement attachment 116 may comprise a distinct housing such as a module housing 120. The depth measurement attachment 116 may be constructed in a manner to minimize the obstruction of the surgeon's view of the surgical site. The depth measurement attachment 116 may further comprise a first sensor 124, such as a displacement sensor that is operably connected to a depth measurement extension 128. As shown, the depth measurement extension 128 is a cannula. The first sensor 124 is configured to output a displacement signal 164 as the depth measurement extension 128 moves relative to the handheld surgical instrument 104. In some configurations, the depth measurement extension 128 has an inner surface 132 that is disposed over a cutting tool 108. Although, in this example, the depth measurement extension 128 is positioned concentrically over the cutting tool 108, in an alternative configuration, the depth measurement extension 128 and the cutting tool 108 do not have to be positioned concentrically. In other configurations, the first sensor 124 may be a depth sensor (e.g., a laser sensor) configured to output the displacement signal 164 as the drill bit moves with respect to the bone. The first sensor 124 may not be housed within the depth measurement attachment 116 and may for example be attached to the handheld surgical instrument 104.

In an example, the depth measurement attachment 116 may comprise a rotatable gear 136. In such an example, the depth measurement extension 128 has a set of rack teeth 140 that are longitudinally disposed over at least a portion of its length which engages the teeth on the rotatable gear 136 by meshing with each other. The rotatable gear 136 which is functionally coupled to the first sensor 124, is operated by any axial movement of the depth measurement extension 128 through the engagement of the rack teeth 140 and teeth on the rotatable gear 136. In this non-limiting example, the first sensor 124 is a potentiometer. Other types of sensors can be used, for instance, an optical sensor, an LVDT sensor, etc.

Figure 4:
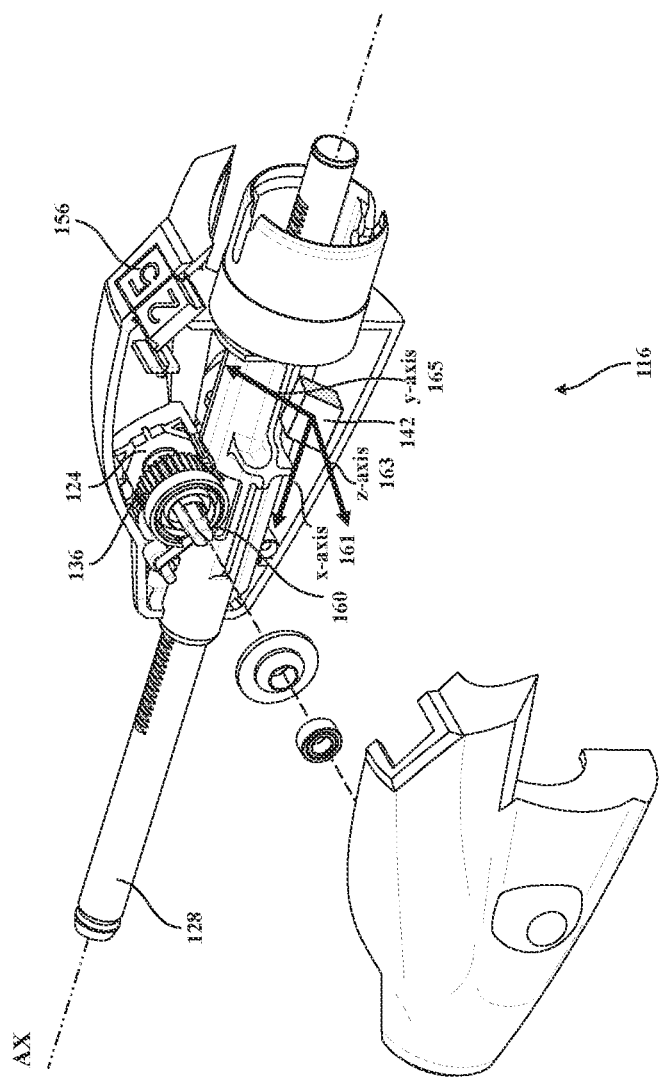
FIG. 4 is a partially exploded view of a depth measurement attachment according to the teachings of the present disclosure.

With reference to FIG. 4, in order to ensure that there is proper function of the depth measurement extension 128 and the first sensor 124, the depth measurement extension 128 may be biased towards an extended position. Through this bias, the distal end of the depth measurement extension 128 always maintains contact with the proximal surface of the bone to be drilled, or the plate/implant which abuts the bone to be drilled. This bias is achieved by use of a spring 160 that biases the rotatable gear 136 in such a way as to rotate the gear in the direction to extend the depth measurement extension 128 distally out of the module housing 120. However, other ways of biasing the depth measure extension 128 relative to the handheld surgical instrument 104 are contemplated. The first sensor 124 is operably connected to the depth measurement extension 128 such that the first sensor 124 is configured to provide a displacement signal 164 over a first time interval 168, discussed in greater detail below.

With reference back to FIG. 3, the depth measurement attachment 116 may further comprise a second sensor 142 configured to output a signal indicative of the motor status. For example, the second sensor 142 may correspond to an accelerometer and may be configured to output a vibration signal indicative of vibration of the motor 114, specifically corresponding to an imbalance of the rotor of the motor 114. In FIG. 2 and FIG. 4, the second sensor 142 is shown disposed inside of the depth measurement attachment 116; however, the second sensor 142 may be positioned at any other suitable location such as inside the handheld surgical instrument 104.

Figure 5:
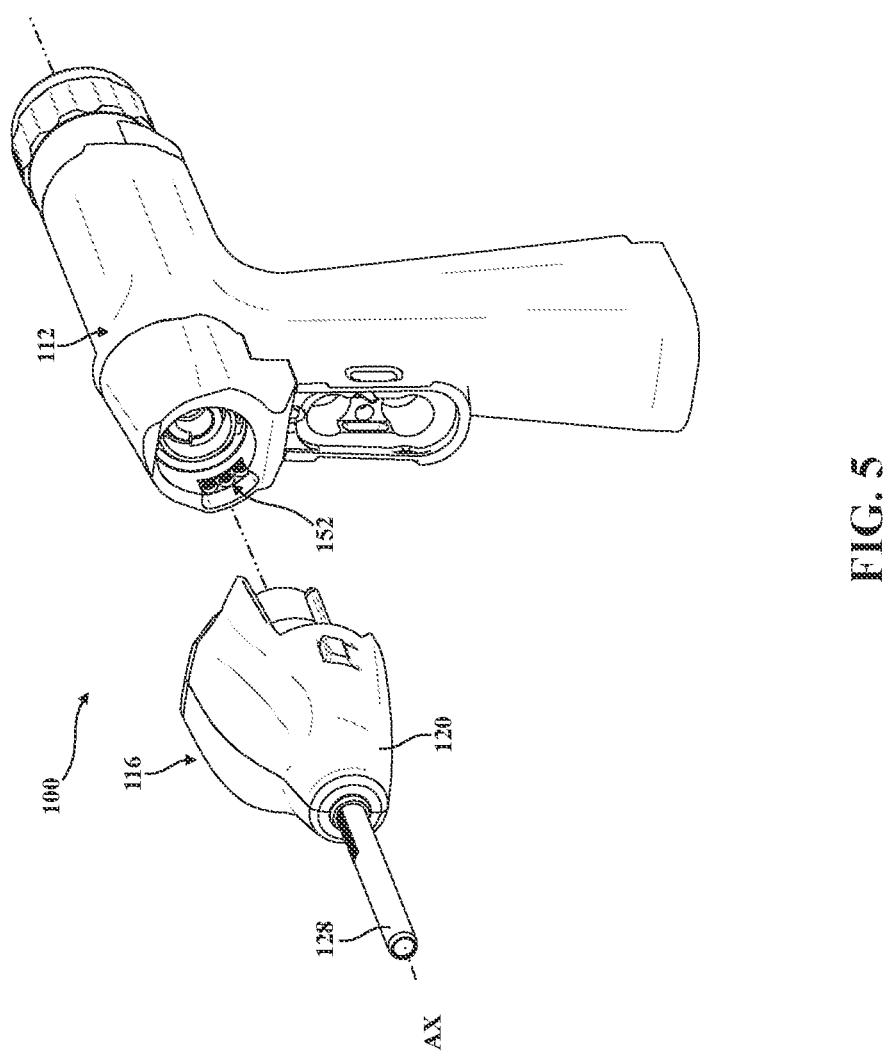
FIG. 5 is a perspective view of a handheld surgical system with a depth measurement attachment separated from an instrument according to the teachings of the present disclosure.
Figure 6:
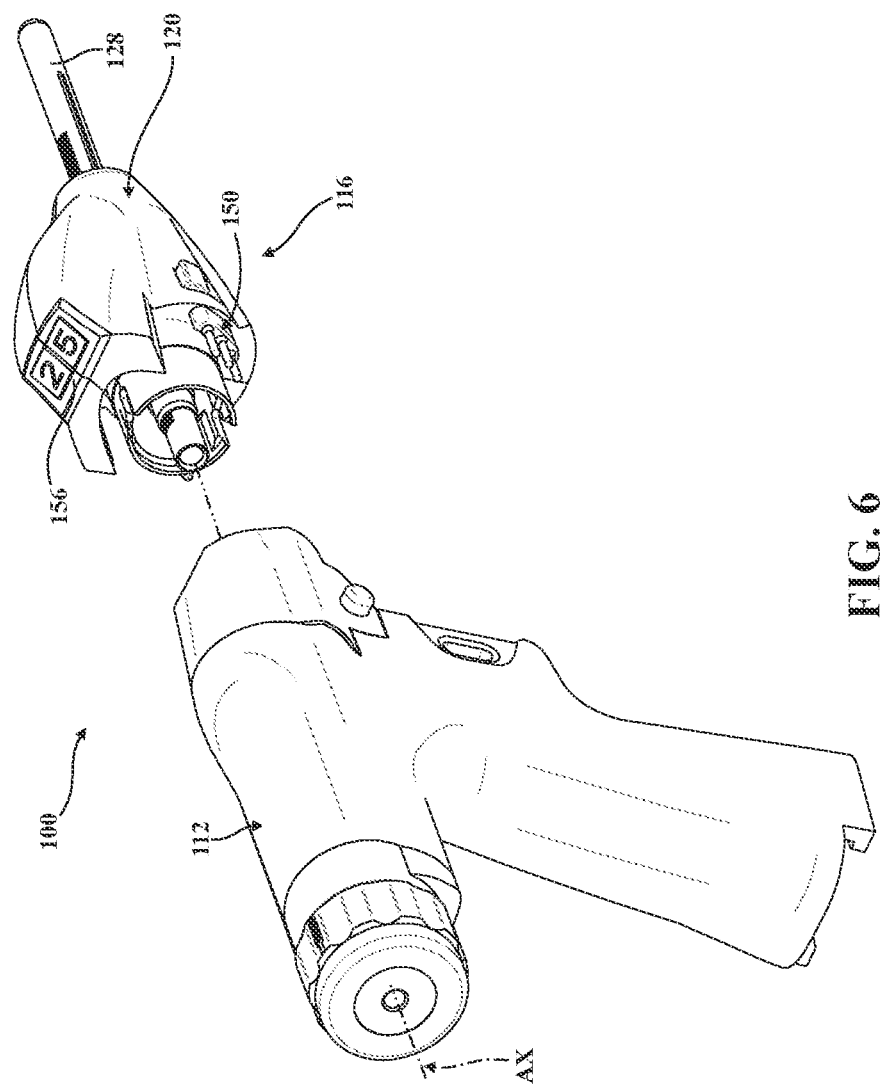
FIG. 6 is a perspective view of a handheld surgical system with a depth measurement attachment separated from an instrument according to the teachings of the present disclosure.

Referring to FIGS. 4 and 5, the depth measurement attachment 116 may include the first controller 144 that is operably connected to the first sensor 124 and the second sensor 142. The first controller 144 may be configured to determine a breakthrough event based on the displacement signal 164 and a vibration signal 166. The breakthrough event may correspond to a time at which a distal end of the drill bit has protruded through a distal cortical wall of a bone of a patient. Based on this time, the first controller 144 may determine the corresponding displacement from the displacement signal 164.

The handheld surgical instrument 104 may also include a second controller 162 that controls operation of the motor 114 of the handheld surgical instrument 104. Although, the first controller 144 and the second controller 162 are shown as separate controllers with the first controller 144 shown disposed within the depth measurement attachment 116 and the second controller 162 being disposed in the handheld surgical instrument 104, the first or second controllers 144, 162 may be housed in a remote device. The first and second controllers 144, 162 may also be integrated into a single controller in instances where there is not a separate depth measurement attachment 116.

The depth measurement attachment 116 may include housing connectors 150 that are configured to operably connect with instrument connectors 152 of the handheld surgical instrument 104. In one example, the handheld surgical instrument 104 may provide the depth measurement attachment 116 with a power signal (a power connection) only via the connection between the instrument connectors 152 and the housing connectors 150. The configuration of the second sensor 142 being disposed within the depth measurement attachment 116 allows for the depth measurement attachment 116 to be able to determine one or more conditions, such as the status or state of the motor 114, associated with the motor 114 without a connection to the second controller 162 of the handheld surgical instrument 104.

In another example, the depth measurement attachment 116 and the handheld surgical instrument 104 may also exchange data via the instrument connectors 152 and the housing connectors 150. The first and second controllers 144, 162 may communicate over a wired connection (i.e., through the housing connectors 150 and the instrument connectors 152) or a wireless connection with each other or other devices. The wireless communications may be facilitated by transceivers located on the first and second controllers 144, 162. These wireless communications transceivers may support protocols such as WI-FI, Bluetooth, or other similar wireless communication protocols. For example, the first and second controllers 144, 162 may send data to a remote device, such as a tablet or external server, which may include a second transceiver.

The depth measurement attachment 116 may also include a display 156, such as a display screen, one or more light-emitting diodes (LEDs), and the like, to provide the surgeon with information relating to movement of the depth cannula, such as to display a real-time drilling depth, a recorded historical maximum drilling depth, a screw length, a breakthrough indication, a cortex drill depth, a bore-hole depth and the like. This same information may also be communicated to the user with a speaker, so as to provide audio indications of the real-time drilling depth, a recorded historical maximum drilling depth, a breakthrough indication and the like.

The depth measurement attachment 116 may include a user input device (not illustrated), such as one or more buttons mounted to the module housing 120 and operatively connected to the first controller 144, the first sensor 124, and/or the second sensor 142. The user input device may control operation of the first sensor 124 and/or the second sensor 142. For example, the user input device may be used to reset, zero, or start signal for the first sensor 124 or the second sensor 142 to start providing displacement data or vibration data to the first controller 144.

Figure 7:
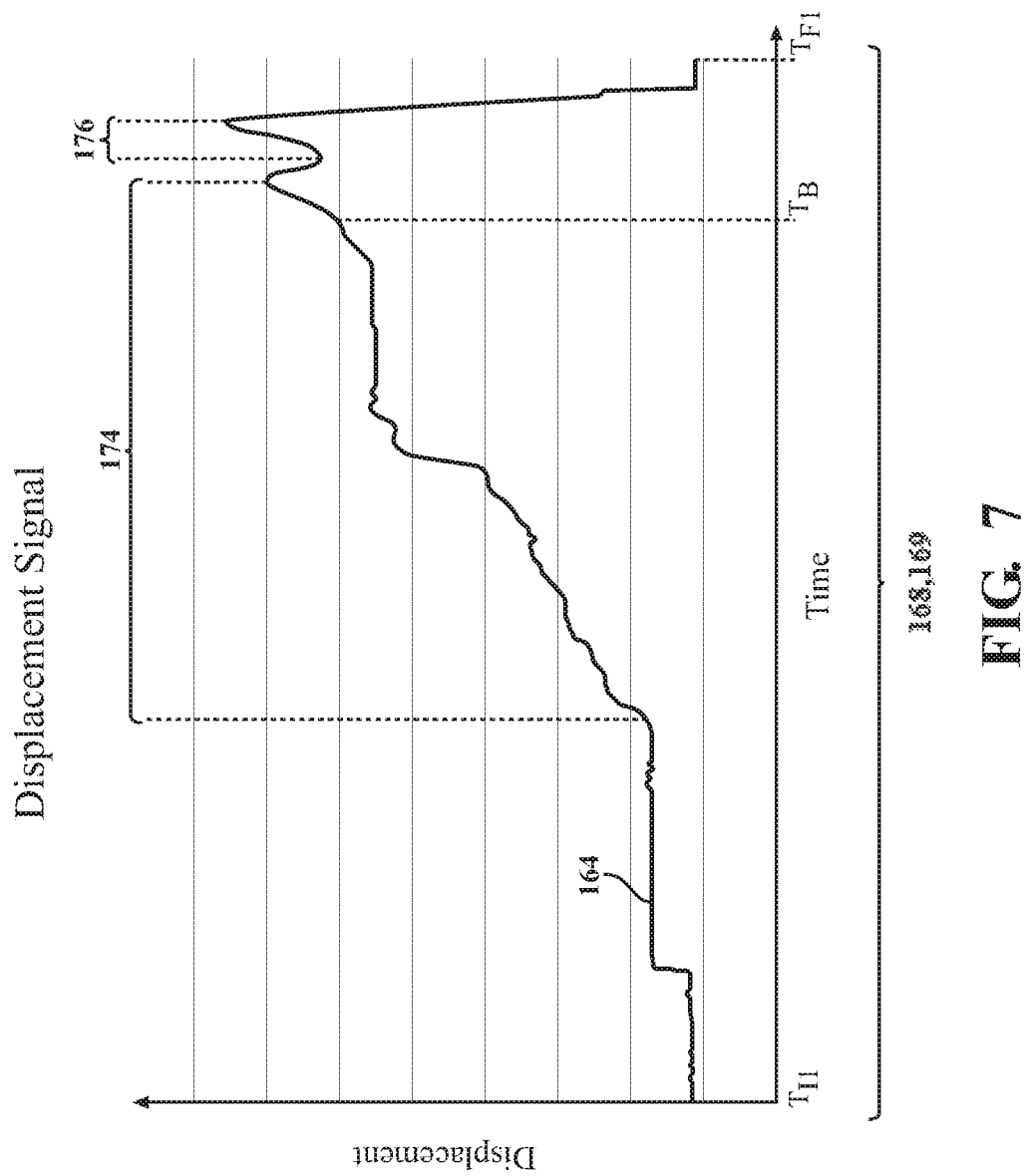
FIG. 7 a graphical representation of a displacement signal corresponding to a surgical drilling process according to the teachings of the present disclosure.

With reference to FIG. 7, the first time interval 168 corresponds to a surgical drilling process. The first time interval 168 is bound by an initial time ($T_{I1}$) and a final time ($T_{F1}$). The user input device may be used to start the first time interval 168, stated differently to set the initial time ($T_{I1}$). That is to say, ($T_{I1}$) is when the surgeon places the drill in position to start a drilling procedure and engages the user input device, and ($T_{F1}$) is when the surgeon fully retracts the drill after performing the particular drilling of the bone such that the depth measurement extension 128 returns to its starting position. At ($T_{I1}$) corresponding to a starting displacement, the depth measurement extension 128 has not been displaced relative to the surgical instrument 104. In an alternative configuration, the first time interval 168 may begin in response to the motor 114 generating rotational torque or based on movement of the depth measurement extension 128.

The displacement data may be collected based on a system clock signal which, in non-limiting examples of a system, clock signals are the internal clock signal of a processor of a controller, or a clock signal from a separate clock device. The system clock signal is used to define the sample rate at which the displacement data is collected and indexed over the first time interval 168 creating the displacement signal 164. It is contemplated that the sample rate may be fixed, or alternatively, the sample rate may be variable, or procedure dependent.

While the illustrated embodiment of the invention shows the second sensor 142 as an accelerometer, various other components may be employed to sense properties indicative of a state of the motor 114 (i.e., whether the motor 114 is generating rotational torque or not) or motor speed external to the instrument. In an alternative configuration, the depth measurement attachment 116 may include an antenna instead of the second sensor 142. With this configuration, the antenna may be configured to receive one or more radio waves generated by the motor 114 when the motor 114 is generating rotational torque. The antenna may be configured to output a voltage signal or a current signal based on the one or more radio waves emitted from the motor 114. The first controller 144 may be configured to receive the voltage signal or current signal and output a motor status signal based on the received one or more radio waves. The first controller 144 may contain signal processing circuitry configured for processing the signal from the antenna and generating the motor status signal. The first controller 144 may then determine whether the motor 114 is generating rotational torque based on the motor status signal.

In another configuration, the second sensor 142 may correspond to an optical sensor configured to detect an optical characteristic of the drill bit, for example, while the drill bit is rotated about the axis AX. Based on the optical characteristic of the drill bit, the optical sensor may output the motor status signal. For example, based on a change in position of the optical characteristic as the drill bit is rotated, evidence by the motor status signal, the first controller 144 may determine that the motor is generating rotational torque. Further details of a configuration of an optical sensor for detecting optical characteristics of a drill bit are discussed in International Application No. PCT/US2020/033288 entitled "Powered Surgical Drill Having Rotating Field Bit Identification" filed on May 15, 2020 is hereby incorporated by reference in its entirety. The optical sensor may include a light source, for example a light emitting diode (LED), configured to emit light onto the drill bit and a transducer to measure a light reflectance of the drill bit. In some configurations, the drill bit may include an optical characteristic such as a laser mark or another distinguishable mark configured to change a parameter of light emitted from the light source.

In another configuration, the second sensor 142 may correspond to a sensor configured to detect a magnetic field, such as a magnetic field sensor, a hall-effect sensor, or a magnetoresistance sensor, emitted by the drill bit while the drill bit is rotated about the axis AX. In this configuration, the drill bit may include one or more magnets or other features configured to emit a magnetic field. The second sensor 142 may be configured to determine the motor status signal based on the detected magnetic field. Based on the motor status signal, the first controller 144 may be configured to determine whether the motor 114 is generating rotational torque. For example, if the magnetic field is varying, the first controller 144 may determine that the motor 114 is generating rotational torque.

In another configuration, the second sensor 142 may correspond to an audio sensor that is configured to detect a characteristic of a sound wave emitted by the motor 114, for example, a sound wave emitted while the motor 114 is generating rotational torque. In some configurations, the audio sensor may correspond to a microphone or another suitable electromechanical transducer. The audio sensor may be configured to determine the motor status signal based on a characteristic of the sound wave. Based on the motor status signal, the first controller 144 may be configured to determine whether the motor 114 is generating rotational torque. For example, the first controller 144 may store one or more characteristics of a previous sound wave generated by the motor 114 and use the stored characteristics in determining whether the motor status signal is representative of the motor 114 generating rotational torque.

In another configuration, the second sensor 142 may correspond to a voltage sensor configured to detect a voltage of the power signal. As previously discussed, the housing connectors 150 of the depth measurement attachment 116 may receive the power signal from the instrument connectors 152. When the motor 114 is generating rotational torque, the voltage of the power signal will include a noise component that is not present when the motor 114 is not generating rotational torque. As such, the first controller 144 may determine whether the motor 114 is generating rotational torque or not based on the voltage of the power signal.

In another configuration, the second sensor 142 may be omitted. In this configuration, the first controller 144 may be configured to determine a frequency component of the displacement signal 164. For example, the first controller 144 may determine the frequency component by performing a Fourier transform of the displacement signal 164. A particular frequency component associated with the motor 114 generating rotational torque may be present in the displacement signal 164 that is not present when the motor 114 is not generating rotational torque. As such, the first controller 144 may be configured to determine whether the motor 114 is generating rotational torque based on the determined frequency component.

In another configuration, a current sensor or other sensor types may be used to determine a status of the motor 114. In such an example, based on the current sensor draw, a first controller 144 may determine whether the motor 114 is generating rotational torque or not. In such a configuration, the data from the current sensor in the handheld surgical instrument 104 must be communicated to the first controller 144. This can be communicated to the first controller 144 via the second controller 162 via a wired or wireless connection.

In another configuration, a sensor may monitor and generate output signals representative of the rotational position of the rotor of the motor 114. One such sensor capable of generating signals representative of this rotor rotational position is a Hall Effect sensor. A Hall Effect sensor generates signals that vary with the sensed magnetic field. The magnetic field adjacent the rotor of the motor 114 is a function of the rotational position of the rotor. Other sensors may generate sensor signals as a function of the operating rate of the motor 114, the temperature of a component of the motor 114, or the voltage applied across the motor 114.

As shown in FIG. 4, the second sensor 142 may be a three-axis accelerometer including an x-axis 161, a y-axis 165, and a z-axis 163; however, it is contemplated that the second sensor 142 may also be a two-axis accelerometer. The accelerometer data is indicative of an inherent imbalance of the rotor of the motor 114. An axis that is parallel to the axis of rotation AX of the motor 114 is less sensitive to the vibration of the motor 114 than an axis that is orthogonal to the axis of rotation AX. Depending on the orientation and position of the second sensor 142, at least one of the x-axis 161, the y-axis 165, or the z-axis 163 may be more sensitive to the imbalance of the rotor of the motor 114 than at least one of the other axes. In FIG. 4, the x-axis 161 is shown as parallel with the axis of rotation AX of the motor 114 while the y-axis 165 and z-axis 163 are shown as orthogonal to the axis of rotation AX of the motor 114. It is contemplated that the second sensor 142 may be positioned or oriented in a different manner such that the y-axis 165 or z-axis 163 are parallel with the axis of rotation AX of the motor 114 and the x-axis is orthogonal to the axis of rotation AX of the motor 114. In some instances, the first controller 144 may implement an algorithm based on the vibration data to determine whether imbalance of the rotor is above a certain threshold or an algorithm based on the vibration data to determine which axis is most sensitive to the imbalance of the rotor.

The first controller 144 may filter the vibration data in various ways. For example, a low-pass filter or a high pass filter may be used to filter out unwanted low or high frequency noise. The filters may be implemented by one or more filter circuits or by software. Based on the vibration data, the first controller 144 generates the vibration signal 166. For example, when the second sensor 142 is an accelerometer, the vibration signal 166 may include an x-axis component, a y-axis component, and a z-axis component. As discussed previously, depending on the orientation of the x-axis 161, the y-axis 165, and the z-axis 163, at least one of the x-axis component, the y-axis component, and the z-axis component will be most sensitive to the vibration of the motor 114.

The vibration data (or other motor status data for alternative configurations of the second sensor 142) may be collected based on an internal clock signal of the processor of the first or second controller 144, 162 or a clock signal from a separate device, such as a clock device associated with the second sensor 142. The clock signal defines the sample rate at which the vibration measurements (or other motor status measurements for alternative configurations) are collected and indexed over a second time interval 169 generating the vibration signal 166 (or motor status signal for alternative configurations). It is contemplated that the sample rate may be fixed, or alternatively, the sample rate may be adjustable, or procedure dependent. In some instances, as illustrated in FIG. 7, the second time interval 169 may correspond to the first time interval 168. In other instances, the second time interval 169 may have a second initial time ($T_{I2}$) and a second final time ($T_{F2}$) that are different from the first initial time ($T_{I1}$) and the first final time ($T_{F1}$). In any instances, at least a portion of the second time interval 169 overlaps some portion of the first time interval 168.

Figure 8:
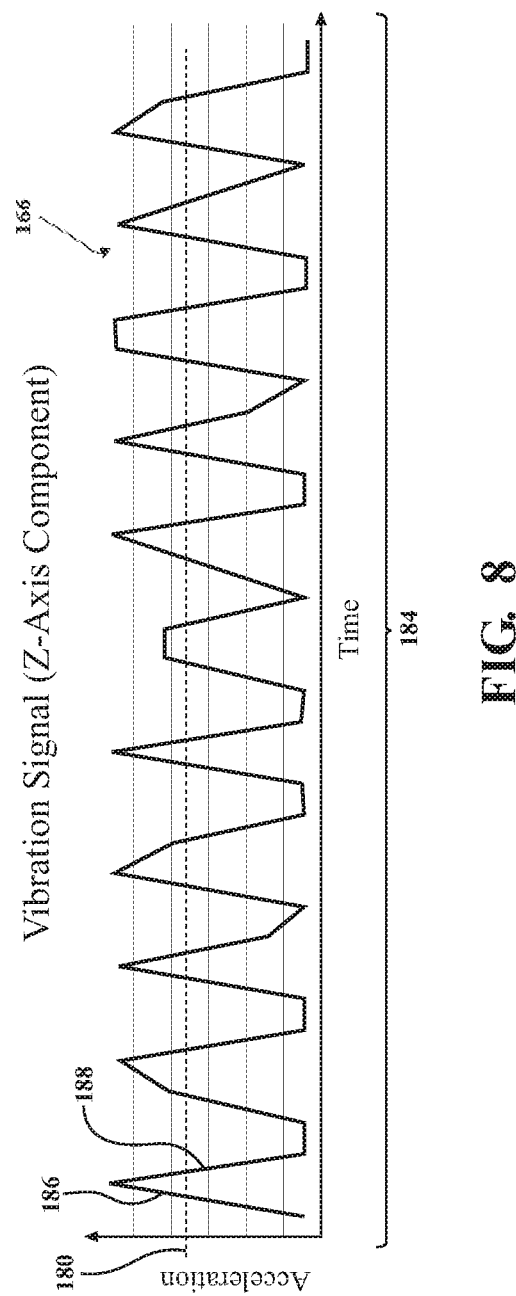
FIG. 8 a graphical representation of a vibration signal corresponding to a surgical drilling process according to the teachings of the present disclosure.

With continued reference to FIGS. 7 and 8, the first controller 144 may determine the status of the motor 114 using one or more algorithms based on the vibration signal 166. The one or more algorithms may be based on the z-axis component over a fifth time interval 184. The fifth time interval 184 may be set to any suitable interval of time. The first controller 144 may divide the first and/or second time intervals 168, 169 by the fifth time interval 184 to establish time blocks. For each time block in the second time interval 169, the first controller 144 may determine the status of the motor 114 based on the vibration signal 166 over the time block.

For example, the first controller 144 may compare the frequency of the z-axis component over the fifth time interval 184 to a first threshold in order to identify whether the motor is in a first state or a second state. The second state may correspond to the motor 114 being on and generating rotational torque, while the first state may correspond to the motor 114 be off and not generating rotational torque. The first threshold may be derived from motor 114 speed such that crossing the first threshold is indicative of the motor 114 transitioning from the first state to the second state at the first threshold.

The frequency may be determined based on a number of increasing and decreasing edges 186, 188 of the vibration signal 166 over the time block. As shown in FIG. 8, a number of increasing and decreasing edges 186, 188 is 22 over the time block. The first controller 144 may be configured to disregard occurrences of the z-axis component below a second threshold 180. In some instances, the first controller 144 may postpone identifying that the motor 114 is in the second state until the frequency of the z-axis component is greater than the first threshold for three successive intervals. In this instance, the first controller 144 may include a counter that is incremented each time the frequency of the z-axis component is greater than the first threshold. Once the counter is greater than a third threshold (e.g., three), the first controller 144 may identify that the motor 114 is in the second state. The third threshold may be adjustable. The first controller 144 may flag time blocks in which the frequency is greater than the first threshold but the counter has not reached the second threshold. If for example, the counter has a value greater than zero but the frequency of the z-axis component falls below the first threshold before the counter reaches the third threshold, the first controller 144 determines that the motor 114 is in the first state and clears the counter.

Figure 9:
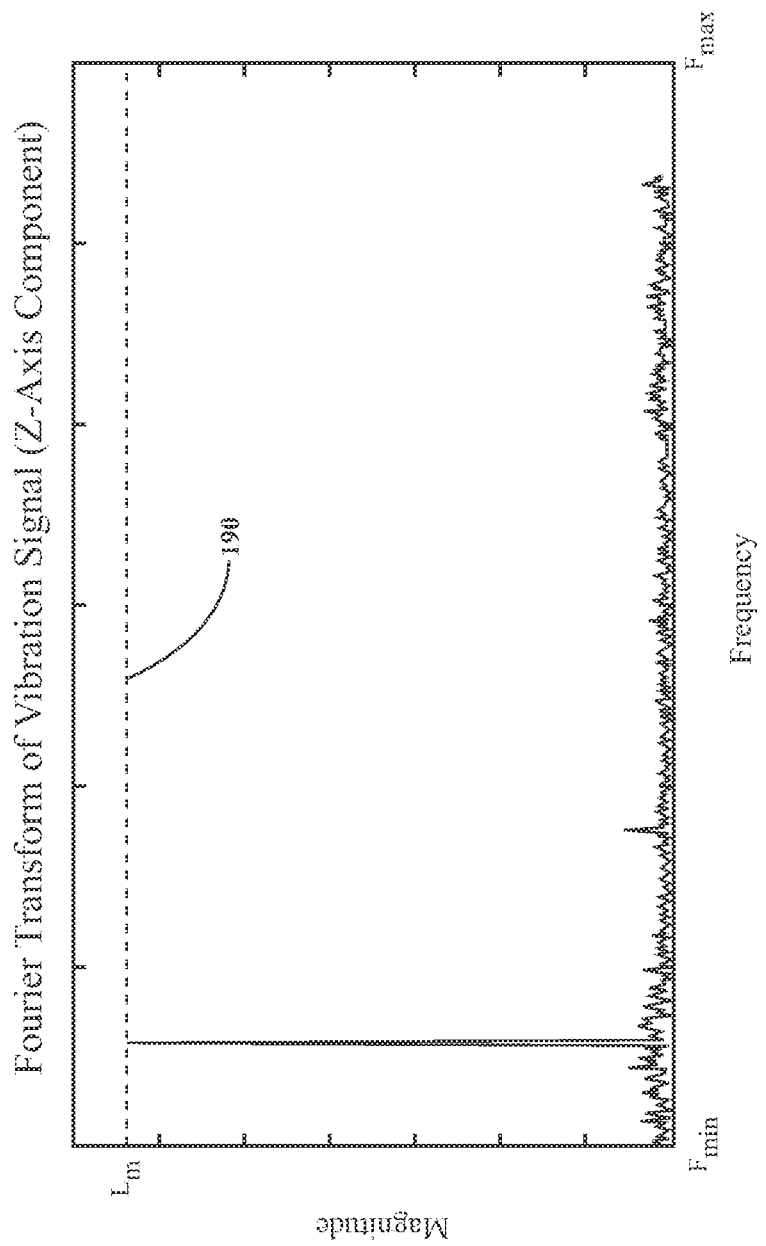
FIG. 9 is a graphical representation of a frequency plot over a frequency range for a time block according to the teachings of the present disclosure.

In another example, the first controller 144 may be configured to determine whether the motor is in the first state or the second state for the time block based on a Fourier transform of the vibration signal 166 over the time block. For example, the first controller 144 may determine a short-time Fourier transform for the z-axis component of the vibration signal 166 for each time block. The short-time Fourier transform may be determined with a fast Fourier transform (FFT) or another suitable algorithm. With reference to FIG. 9, a frequency plot of the Fourier transform of the vibration signal 166 over a respective time block is shown. In FIG. 9, a full range of frequency bins are shown. The range of frequency bins is defined by a minimum frequency bin ($F_{Min}$) and a maximum frequency bin ($F_{Max}$). The width for each frequency bin may be defined by Equation 1:

$$B_w = S_f / T_s \qquad \text{(Equation 1)}$$

where $B_w$ represents the bin width, $S_f$ represents the sampling frequency, and $T_s$ represents the total number of samples.

Figure 10:
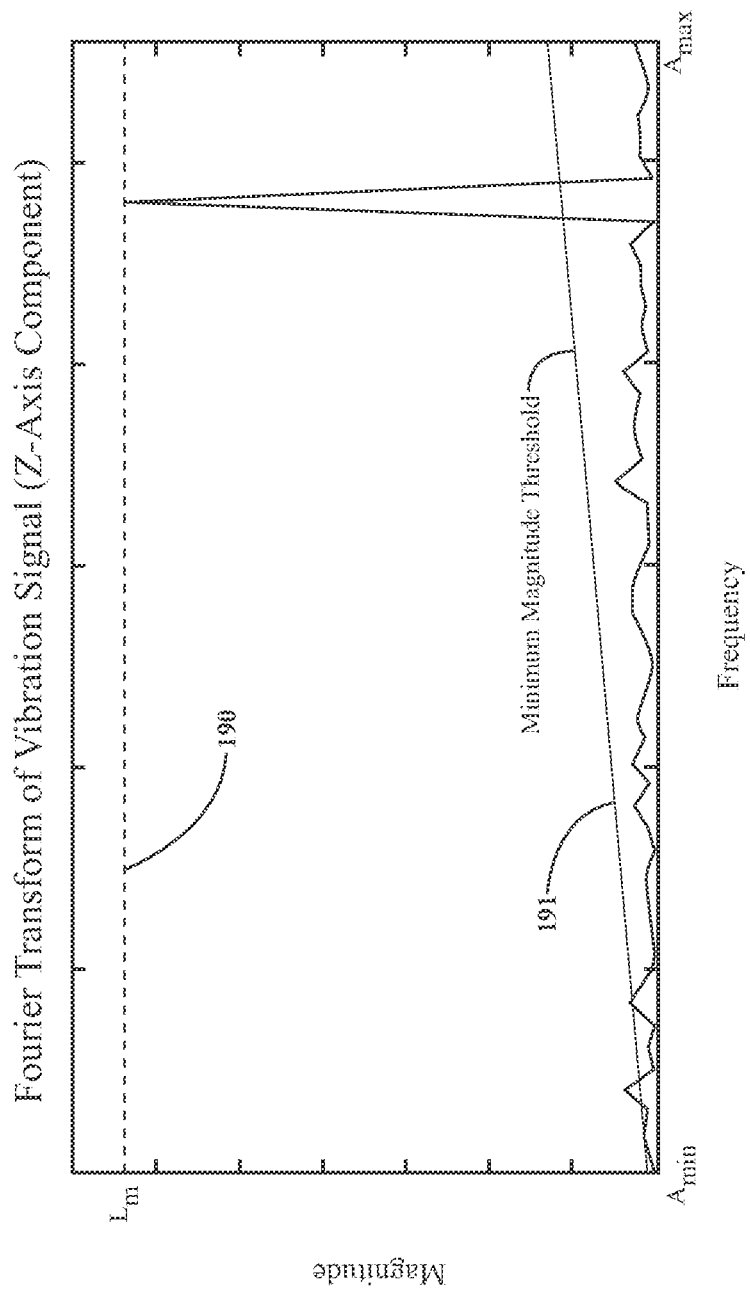
FIG. 10 is a graphical representation of a frequency plot over a narrower frequency range for a time block according to the teachings of the present disclosure.

The first controller 144 may be configured to adjust the range of frequency bins such that higher frequencies (e.g., frequencies greater than 330 hertz) and lower frequencies (frequencies less than 50 hertz) are not considered when determining motor status for a time block. In FIG. 10, a frequency plot for a Fourier transform with an adjusted frequency range is shown. The frequency range is bounded by an adjusted minimum frequency bin ($A_{Min}$) and an adjusted maximum frequency bin ($A_{Max}$).

For each frequency bin, the first controller 144 may compare the magnitude of the frequency bin to a minimum magnitude threshold 191. If the magnitude of the frequency bin is greater than the minimum magnitude threshold 191, the first controller 144 may then compare the magnitude for the frequency bin to other bins that satisfy the minimum magnitude threshold 191 condition. When the first controller 144 determines for two consecutive time blocks that the frequency bins are the same, the first controller 144 may determine that the motor is set to the second state for the consecutive time blocks and any flagged time blocks. When the first controller 144 determines for a time block that none of the frequency bins have a magnitude greater than the minimum magnitude threshold 191, the first controller 144 may determine that the motor 114 is set to the first state for the time block.

Various breakthrough algorithms are contemplated that determine a breakthrough event (i.e., a breakthrough time ($T_B$) at which the drill breaks through the distal cortical wall) based on patterns in the displacement signal 164 over time. The first controller 144 may implement the various breakthrough algorithms based on the displacement signal 164 and the vibration signal 166 to determine the breakthrough time ($T_B$). The first controller 144 may be configured to derive and store other signals based on the displacement signal 164 such as a velocity-related signal and acceleration-related signal. Based on the starting displacement and the breakthrough time ($T_B$), the first controller 144 may determine corresponding breakthrough displacement at the breakthrough time ($T_B$).

The breakthrough algorithms may be optimized by primarily collecting only data associated with a procedural displacement, such as displacement of the depth measurement extension 128 during the actual surgical drilling procedure, for example, while the surgeon is drilling through the bone. Non-procedural displacement occurs when the depth measurement extension 128 is displaced when the motor 114 is off or operating at a non-cutting speed and the surgeon is not actually drilling through the bone. Non-procedural events, that lead to non-procedural displacement, may cause the displacement signal 164 to mimic a pattern that the first controller 144 associates with the breakthrough time ($T_B$). Thus, the first controller 144 may falsely identify the breakthrough time ($T_B$) during one of these non-procedural displacement portions of the displacement signal 164. It may be difficult to distinguish non-procedural displacement of the displacement signal 164 from procedural displacement of the displacement signal 164 using existing breakthrough detection algorithms; thus, additional systems and methods for distinguishing non-procedural displacement from procedural displacement may improve the accuracy of breakthrough detection. The handheld surgical system 100 may also exhibit improved processing times for breakthrough detection when the algorithm needs to primarily process only procedural data.

The first controller 144 may also be configured to determine one or more procedural events (i.e., events associated with procedural displacement) from the displacement signal 164 or other signals derived from the displacement signal 164 such as a velocity-related signal or acceleration-related signal. The one or more procedural events may also refer to changes in acceleration, displacement, and or velocity determined from the displacement signal 164, for example, a maximum displacement, a local maximum displacement, a minimum displacement, a local minimum displacement, a maximum acceleration, a local maximum acceleration, a maximum velocity, a local maximum velocity, a minimum velocity, a local minimum velocity, and a slope having a value exceeding a predetermined threshold.

Non-procedural displacement may be the result of accidental events. The accidental events may include manual manipulation of the depth measurement extension 128. Manual manipulation may be unintentional and occur when the surgeon or other medical personnel displaces the depth measurement extension 128 prior to the start of the drilling procedure, during the drilling procedure or after the drilling procedure, when the motor 114 is off.

The status of the motor 114 may be used to distinguish procedural displacement from non-procedural displacement. In FIG. 7, procedural displacement is indicated over a third time interval 174, while non-procedural displacement is shown over a fourth time interval 176. The first controller 144 may determine and store one or more events associated with the drilling procedure based on the vibration signal 166 and the displacement signal 164. The one or more events may include, but are not limited to, a status of the motor 114 throughout the drilling procedure, a speed of the motor 114 throughout the drilling procedure, the starting displacement, the breakthrough displacement, the breakthrough time ($T_B$), the drill start time, and the drill end time. The first controller 144 may determine the drill bore-depth based on the one or more events associated with the surgical drilling procedure and then subsequently determine a suitable screw length for fixation to the bone based on the drill bore-length.

Figure 11:
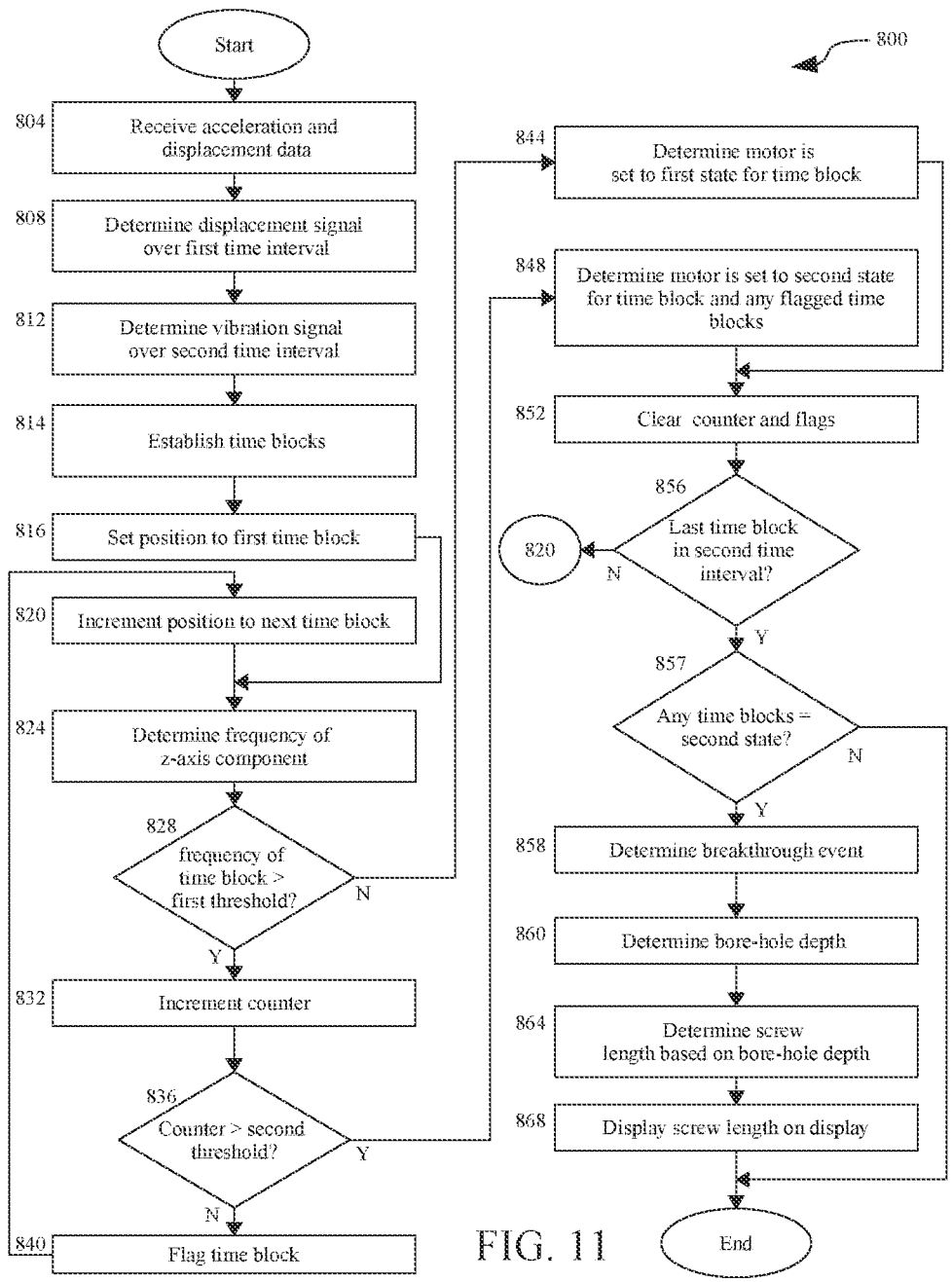
FIG. 11 is an exemplary flowchart performed by a controller of a handheld surgical system according to the teachings of the present disclosure.

With reference to FIG. 11, the method 800 may be performed by the first controller 144. At 804, the method 800 begins where the first controller 144 receives the displacement data and vibration data. At 808, the first controller 144 determines the displacement signal 164 over the first time interval 168. At 812, the first controller 144 determines the vibration signal 166 over the second time interval 169. At 814, the first controller 144 establishes time blocks by dividing the second time interval 169 by the fifth time interval 184 and the method 800 continues at 816. At 816, the first controller 144 sets a pointer position to the first time block of the second time interval 169 and the method 800 continues at 824.

At 824, the first controller 144 determines the frequency of the z-axis component over the time block and control continues to 828. At 828, the first controller 144 determines whether the frequency of the z-axis component for the time block is greater than the first threshold. If so, the method 800 continues to 832; otherwise, the method 800 continues at 844. At 844, the first controller 144 determines that the motor 114 is set to the first state for the time block and the method 800 continues at 852. At 832, the first controller 144 increments a counter and the method 800 continues to 836.

At 836, the first controller 144 compares a value of the counter to the second threshold. If the value of the counter is greater than the second threshold, the method 800 continues at 848; otherwise, the method 800 continues to 840. At 840, the first controller 144 flags the time block and the method 800 continues back at 820. At 820, the first controller 144 increments the pointer position to the next time block and the method 800 continues back to 824.

At 848, the first controller 144 determines that the motor 114 is set to the second state and the method 800 continues to 852. At 852, the first controller 144 clears the counters and the flags. At 856, the first controller 144 determines whether the current time block is the last time block in the second time interval 169. If so, the method 800 continues at 857; otherwise, the method 800 continues back to 820. At 857, the first controller 144 determines whether the status of the motor 114 for any of the time blocks is set to the second state. If so, the method continues at 858; otherwise, the method may end.

At 858, the first controller 144 determines the breakthrough event (i.e., the breakthrough time ($T_B$)) based on status of the motor 114 and displacement signal 164 and the method 800 continues at 860. At 860, the first controller 144 determiners a bore-hole depth based on the displacement of the depth measurement extension 128 at the breakthrough time ($T_B$) and the method 800 continues at 864. At 864, the first controller 144 determines a screw length based on the drill bore-hole depth. At 868, the first controller 144 transmits a screw length to the display 156. While the example is provided that one of the controller transmits the screw length for display on the display 156, the first controller 144 may transmit the screw length to another controller such as a controller associated with a remote device so that the remote device may display the screw length.

Figure 12:
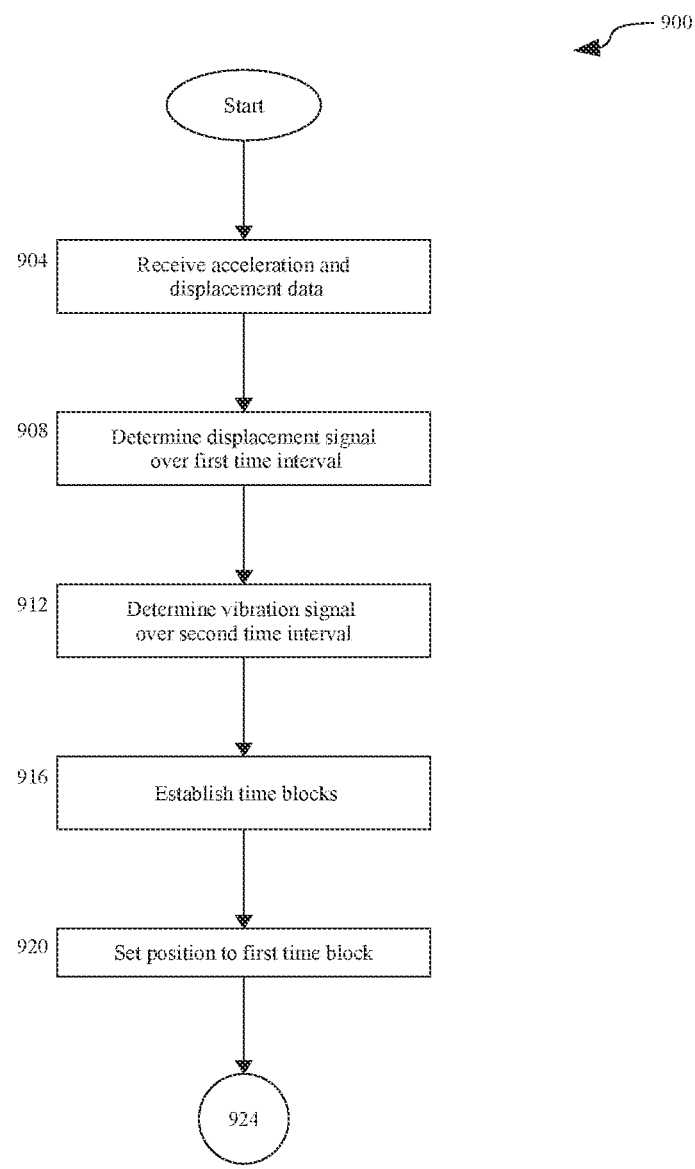
FIGS. 12-14 are exemplary flowcharts performed by a controller of a handheld surgical system according to the teachings of the present disclosure.

With reference to FIG. 12, the method 900 may be performed by the first controller 144. At 904, the method 900 begins where the first controller 144 receives the displacement data and vibration data. At 908, the first controller 144 determines the displacement signal 164 over the first time interval 168. At 912, the first controller 144 determines the vibration signal 166 over the second time interval 169. At 916, the first controller 144 establishes time blocks by dividing the second time interval 169 by the fifth time interval 184 and the method 900 continues at 916. At 916, the first controller 144 sets a pointer position to a first time block and the method 900 continues at 924 of FIG. 12.

At 924, the first controller 144 performs a Fourier transform of the vibration signal 166 over the time block. At 926, the first controller 144 adjusts the frequency bin range. At 928, the first controller 144 sets a pointer position to a first bin of the adjusted frequency range and the method 900 continues at 936. At 936, the first controller 144 determines whether a magnitude of the frequency bin is greater than the minimum magnitude threshold 191 for the bin. If so, control continues at 940; otherwise, control continues at 930. At 940, the first controller 144, determines whether the current bin is the first bin in the range with a magnitude that is greater than the minimum magnitude threshold 191. If so, control may continue at 944; otherwise control may continue at 948. At 944, the first controller 144 sets the bin as the maximum bin (max_bin) with the associated magnitude. At 946, the first controller 144 determines if the bin is that last bin in the frequency range. If so, control continues at 956; otherwise, control continues back at 932.

Figure 14:
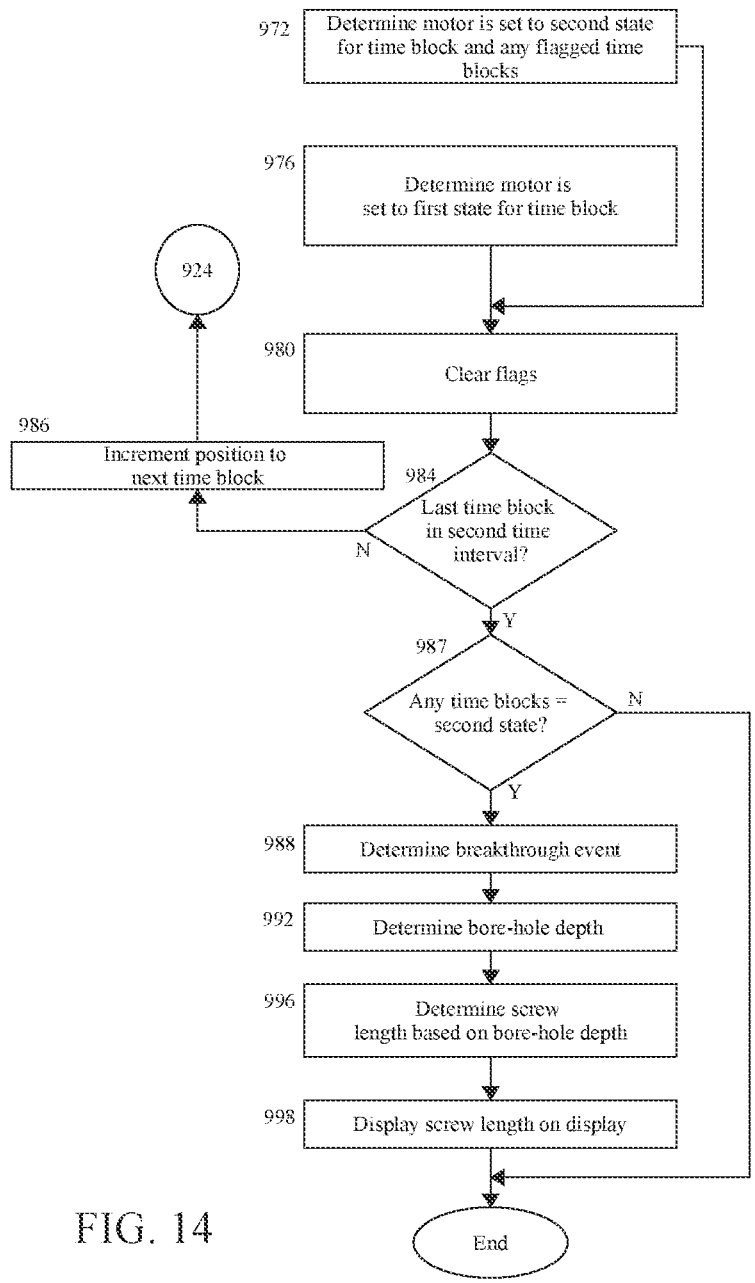

At 930, the first controller 144 determines whether the bin is the last bin in the frequency range. If so, the method 900 continues at 931. Otherwise, the method 900 continues at 932. At 931, the first controller 144 determines whether the max_bin has been set. If so, control continues at 956; otherwise, control continues back at 976 of FIG. 14. At 932, the first controller 144 increments the pointer position to the next bin and control continues to 936.

At 948, the first controller 144 determines if the magnitude of the bin is greater than the magnitude of max_bin. If so, control continues at 944; otherwise control continues at 952. At 952, the first controller 144, determines whether the bin is the last bin in the frequency range. If so, the method 900 continues at 956; otherwise, the method 900 continues at 932. At 956, the first controller 144 sets and stores motor_status_freq for the time block to the frequency bin associated with the max_bin. At 960, the first controller clears the max_bin. At 964, the first controller 144 determines whether the motor_status_freq of the time block matches the motor_status_freq of the previous time block. If so, the method 900 continues at 972 of FIG. 14; otherwise, the method 900 continues at 968. At 968, the first controller 144 flags the time block and the method 900 continues at 984.

Figure 13:
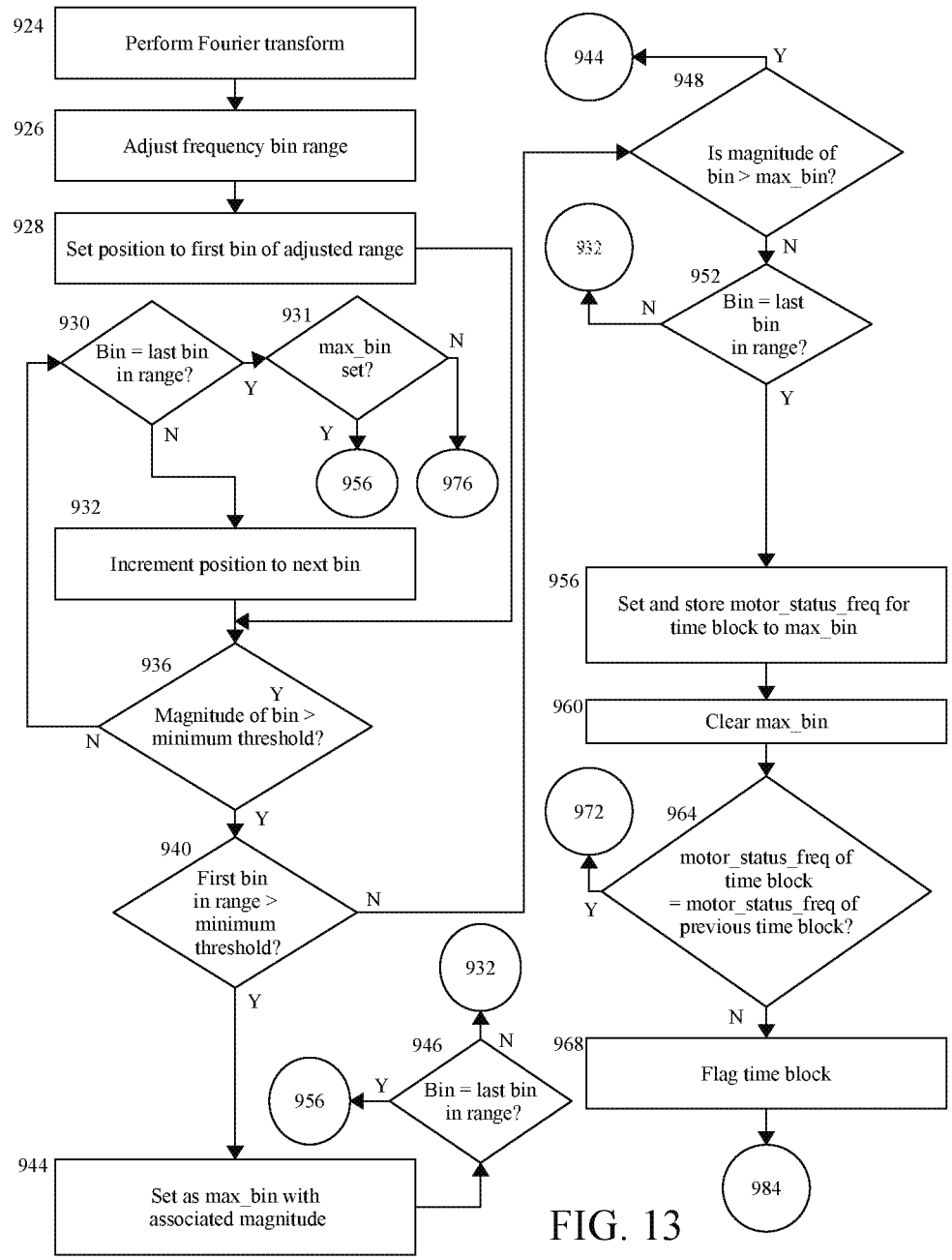

At 972, the first controller 144 determines that the motor 114 is set to the second state for the time block and any flagged time blocks and the method 900 continues to 980. At 976, the first controller 144 determines that the motor 114 is set to the first state for the time block and the method 900 continues to 980. At 980, the first controller 144 clears the flags. At 984, the first controller 144 determines whether the time block is the last time block in the second time interval 169. If so, the method 900 continues at 987; otherwise, the method 900 continues at 986. At 986, the first controller 144 increments the pointer position to the next time block and the method 900 continues back at 924 of FIG. 13. At 987, the first controller 144 whether the status of the motor 114 for any of the time blocks is set to the second state. If so, the method 900 continues at 988; otherwise, the method 900 may end.

At 988, the first controller 144 determines the breakthrough event (i.e., the breakthrough time ($T_B$)) based on the status of the motor 114 and displacement signal 164 and the method 900 continues at 992. At 992, the first controller 144 determines a bore-hole depth based on the displacement of the depth measurement extension 128 at the breakthrough time ($T_B$) and the method 900 continues at 996. At 996, the first controller 144 determines a screw length based on the drill bore-hole depth. At 998, the first controller 144 transmits a screw length to the display 156. While the example is provided that one of the controllers transmits the screw length for display on the display 156, the first controller 144 may transmit the screw length to another controller such as a controller associated with a remote device so that the remote device may display the screw length.

Clauses

Clause 1—A handheld surgical system for determining a suitable screw length for bone fixation, the handheld surgical system comprising: a housing; a motor positioned in the housing; a depth measurement attachment that is removably coupled to the housing, the depth measurement attachment comprising: a first sensor configured to provide a displacement signal corresponding to a drilling process; and a second sensor configured to provide a vibration signal associated with a vibration of the motor corresponding to the drilling process; and a controller configured to: receive the vibration signal and the displacement signal; and determine (i) one or more characteristics associated with the motor, based on the vibration signal, using an algorithm, (ii) a breakthrough event based on the one or more characteristics associated with the motor and the displacement signal, and (iii) the suitable screw length based on the breakthrough event and the displacement signal.

Clause 2—A surgical device comprising: a housing; a motor positioned within the housing; a first sensor configured to generate a motor status signal associated with the motor during a drilling process; a second sensor configured to provide a displacement signal associated with a displacement of a drill bit during the drilling process; and a controller configured to: receive the motor status signal and the displacement signal; determine one or more characteristics of the motor, based on the motor status signal, using a predetermined algorithm; and determine a breakthrough event based on a status of the motor and the displacement signal.

Clause 3—The surgical device of clause 2, wherein the one or more characteristics of the motor include a state of the motor and a speed of the motor. 1-1

Clause 4—The surgical device of clause 2, wherein the controller is further configured to calculate a suitable screw length based on the breakthrough event and the displacement signal.

Clause 5—A depth measurement attachment for sending a drill depth for a handheld surgical system, wherein the handheld surgical system comprises an instrument including a housing and a motor positioned in the housing, the depth measurement attachment comprising: a component configured to generate a displacement signal associated with a displacement of a drill bit during a drilling process; and a controller configured to: receive the displacement signal; determine a frequency component of the displacement signal; determine whether the motor is generating rotational torque, based on the frequency component; and determine a breakthrough event based on the frequency component and the displacement signal.

Clause 6—A handheld surgical system comprising: an instrument comprising: a housing; and a motor positioned in the housing; a depth measurement attachment that is removably coupled to the instrument, the depth measurement attachment comprising: a component configured to output a motor status signal associated with the motor during a drilling process; and a displacement sensor configured to output a displacement signal associated with a displacement of a drill bit during the drilling process; and a controller configured to: receive the motor status signal and the displacement signal; determine whether the motor is generating rotational torque, based on the motor status signal; and determine a breakthrough event based on the motor status signal and the displacement signal.

Clause 7—A depth measurement attachment for sending a drill depth for a handheld surgical system, wherein the handheld surgical system comprises an instrument including a housing and a motor positioned in the housing, the depth measurement attachment comprising: a first sensor configured to output a vibration signal associated with a vibration of the motor during a drilling process; and a second sensor configured to output a displacement signal associated with a displacement of a drill bit during the drilling process; and a controller configured to: receive the vibration signal and the displacement signal; determine whether the motor is generating rotational torque, based on the vibration signal; and determine a breakthrough event based on the vibration signal and the displacement signal.

Clause 8—A handheld surgical instrument comprising: a housing; and a motor positioned in the housing, the motor configured to apply rotational torque to a drill bit during a drilling process; a first sensor configured to output a motor status signal associated with the motor during the drilling process; and a second sensor configured to output a displacement signal associated with a displacement of the drill bit during the drilling process; and a controller configured to: receive the motor status signal and the displacement signal; determine whether the motor is generating the rotational torque, based on the motor status signal; and determine a breakthrough event based on the motor status signal and the displacement signal.

Clause 9—A method for determining a breakthrough event of a drilling process, the method comprising: sensing data, with a first sensor and a second sensor, indicative of one or more procedural events and one or more non-procedural events of the drilling process, wherein: the one or more procedural events are associated with movement of a drill bit relative to a bone of a patient when a motor is generating rotational torque, and the one or more non-procedural events are associated with movement of the drill bit relative to the bone of the patient when the motor is off; determining whether the data corresponds to the one or more procedural events or the one or more non-procedural events; and determining the breakthrough event based on the data associated with the one or more procedural events.

Clause 10—A method for determining a breakthrough event of a drilling process with a depth measurement attachment for sending a drill depth for a handheld surgical system including an instrument with a housing and a motor configured to apply rotational torque to a drill bit positioned in the housing, the depth measurement attachment including a component, a second sensor, and a controller, the method comprising: outputting, with the component, a motor status signal associated with the motor during the drilling process; outputting, with the second sensor, a displacement signal associated with a displacement of the drill bit during the drilling process; and receiving, with the controller, the motor status signal and the displacement signal; determining, with the controller, whether the motor is generating the rotational torque, based on the motor status signal; and determining, with the controller, the breakthrough event based on the motor status signal and the displacement signal.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A handheld surgical system comprising:
   an instrument comprising:
      a housing;
      a first electrical connector; and
      a motor positioned within the housing;
   a depth measurement attachment that is removably coupled to the instrument, the depth measurement attachment comprising:
      a second electrical connector configured to receive electrical power via a power signal from the first electrical connector of the instrument;
      a component comprising a first sensor configured to detect a voltage of the power signal, and the component configured to output a motor status signal associated with the motor based on the voltage of the power signal during a drilling process;
      a second sensor configured to provide a displacement signal associated with a displacement of a drill bit during the drilling process;
   memory;
   a controller; and
   one or more programs, wherein the one or more programs are stored in the memory and configured to be executed by the controller, the one or more programs including instructions for:
      receiving the motor status signal and the displacement signal;
      determining whether the motor is generating rotational torque, based on the motor status signal; and
      determining a breakthrough event based on the motor status signal and the displacement signal.

2. The handheld surgical system of claim 1, wherein the controller is further defined as a first controller, the handheld surgical system further comprising a second controller configured to control operation of the motor, and wherein the first controller is disposed inside of the depth measurement attachment.

3. The handheld surgical system of claim 1, further comprising a depth measurement extension that is operably coupled to the depth measurement attachment.

4. The handheld surgical system of claim 3, wherein the second sensor is connected to the depth measurement extension to provide the displacement signal based on a position of the depth measurement extension.

5. The handheld surgical system of claim 1, wherein:
   the depth measurement attachment includes a user input device;
   the displacement signal is provided over a displacement time interval; and
   the displacement time interval begins in response to the user input device being engaged.

6. The handheld surgical system of claim 1, wherein:
   the displacement signal is provided over a displacement time interval; and
   the displacement time interval begins when the motor begins to run and ends when a surgeon fully retracts the drill bit from a bone of a patient.

7. The handheld surgical system of claim 1, wherein the one or more programs are further configured to determine a suitable screw length based on the breakthrough event and the displacement signal.

8. The handheld surgical system of claim 1, wherein:
   the one or more programs are further configured to determine procedural displacement and non-procedural displacement from the displacement signal;
   the procedural displacement is associated with displacement when the motor is generating rotational torque; and
   the non-procedural displacement is associated with displacement when the motor is not generating rotational torque.

9. The handheld surgical system of claim 1, wherein the one or more programs are further configured to determine a procedural event based on the displacement signal.

10. The handheld surgical system of claim 9, wherein the procedural event corresponds to a maximum displacement, a local maximum displacement, a minimum displacement, a local minimum displacement, a maximum acceleration, a local maximum acceleration, a maximum velocity, a local maximum velocity, a minimum velocity, a local minimum velocity, and a slope having a value exceeding a predetermined threshold.

11. A depth measurement attachment for sending a drill depth for a handheld surgical system, wherein the handheld surgical system comprises an instrument including a housing and a motor positioned in the housing, the depth measurement attachment comprising:
   an electrical connector configured to receive electrical power via a power signal from a complementary electrical connector of the instrument;
   a component comprising a first sensor configured to detect a voltage of the power signal, and the component configured to output a motor status signal associated with the motor based on the voltage of the power signal during a drilling process;
   a second sensor configured to output a displacement signal associated with a displacement of a drill bit during the drilling process;

memory;
a controller; and
one or more programs, wherein the one or more programs are stored in the memory and configured to be executed by the controller, the one or more programs including instructions for:
receiving the motor status signal and the displacement signal;
determining whether the motor is generating rotational torque, based on the motor status signal; and
determining a breakthrough event based on the motor status signal and the displacement signal.

* * * * *